United States Patent [19]
Edlind et al.

[11] Patent Number: 5,434,163
[45] Date of Patent: Jul. 18, 1995

[54] TREATMENT OF CRYPTOCOCCUS NEOFORMANS INFECTION

[75] Inventors: Thomas D. Edlind, Wyndmoor; Maria C. Cruz, Philadelphia, both of Pa.

[73] Assignee: The Medical College of Pennsylvania, Philadelphia, Pa.

[21] Appl. No.: 62,444

[22] Filed: May 14, 1993

[51] Int. Cl.$^6$ .............................................. A61K 31/47
[52] U.S. Cl. .................................. 514/310; 514/226.8; 514/393; 514/395; 514/365; 514/31; 546/143; 546/144; 546/145; 546/194; 546/201; 546/210; 546/300
[58] Field of Search ............. 514/310, 232, 226.8, 514/393; 546/143, 144, 145, 194, 201, 210, 300

[56] References Cited

U.S. PATENT DOCUMENTS

| | | | |
|---|---|---|---|
| 3,745,187 | 7/1973 | Naguchi et al. | 514/310 |
| 3,769,308 | 10/1973 | Kohmoto et al. | 514/310 |
| 4,725,605 | 2/1988 | Crossley et al. | 514/338 |
| 4,794,123 | 12/1988 | Crossley et al. | 514/232 |
| 4,863,945 | 9/1989 | Crossley et al. | 514/393 |
| 4,952,589 | 8/1990 | Brown | 514/310 |
| 5,061,715 | 10/1991 | Sunkara | 514/314 |
| 5,151,426 | 8/1991 | Bellene | 514/262 |
| 5,200,417 | 4/1993 | Brown et al. | 514/310 |

*Primary Examiner*—Werren B. Lone
*Attorney, Agent, or Firm*—Janice E. Williams; Edward T. Lentz

[57] ABSTRACT

A method of treatment of *Cryptococcus neoformans* infection by administering to a patient in need thereof an effective amount of a benzimidazile compound.

6 Claims, No Drawings

TREATMENT OF CRYPTOCOCCUS NEOFORMANS INFECTION

BACKGROUND OF THE INVENTION

The present invention relates to the use of benzimidazole anthelmintics in the treatment of cryptococcal infection including meningitis in particular in AIDS patients, including individuals exhibiting HIV infection as well as auto-immune deficiency syndrome.

*Cryptococcus neoformans* is an encapsulated yeast that causes meningitis in AIDS patients. Currently recommended therapy includes amphotericin B+/−flucytosine. Toxicity is high and relapses are common. Benzimidazoles are a large group of drugs used clinically for helminth infections and agriculturally as antifungal agents. There exists a need for additional or better therapies for treatment of *Crytococcus neoformans*.

DETAILED DESCRIPTION OF THE INVENTION

It has now been found that certain benzimidazole anthelmintics also have in vitro activity against *Cryptococcus neoformans* and as such are expected to be of use in the treatment of infections caused by this organism. More specifically the compounds are expected to be of use in the treatment of meningitis caused by this organism in particular in patients having AIDS.

In particular, fenbendazole, albendazole and mebendazole have been found to exhibit high levels of activity against the organism and are the preferred benzimidazole derivatives of the present invention. Those skilled in the an will recognize that other benzimidazole anthelmintics and their derivatives may exhibit activity against *Cryptococcus neoformans* as well and may be substituted for the preferred embodiment of the present invention.

The presently most preferred benzimidazoles for the composition of the invention are fenbendazole [methyl 5-(phenylthio)-1H-benzimidazol-2-ylcarbamate], albendazole [methyl 5-(n-propylthio)-1H-benzimidazol-2-ylcarbamate] and mebendazole. However, it is possible to substitute other known and commercially available benzimidazoles or prodrugs which metabolize into a suitable benzimidazole. Among such compounds are oxibendazole [methyl 5-(n-propoxy)-1H-benzimidazol-2-ylcarbamate], oxfendazole [methyl 5-(phenylsulfinyl)-1H-benzimidazole-2-ylcarbamate], parbendazole, cambendazole, flubendazole, ricobendazole, luxabendazole and others. These benzimidazole are commercially available.

Prodrugs which metabolize in vitro into selected benzimidazoles may also be employed to replace the preferred benzimidazoles in the compositions of this invention. Among the known prodrugs are thiophanates [1,2-phenylenebis (iminocarbonothioyl) biscarbamic acid diethyl esters]. See, for example, U.S. Pat. Nos. 3,745,187 and 3,769,308. Another prodrug which may be useful is Febantel, i.e., [2-[(methoxyacetyl) amino]-4-(phenylthio)-phenyl]carbonimidoyl] biscarbamic acid dimethyl ester. Also useful may be the Netobimin esters. These known compounds may also be prepared by known and conventional methods by one of skill in the art.

When used in the method of the invention, the benzimidazole compound is formulated in a standard pharmaceutical composition such as a tablet using standard formulation methods and techniques.

It is expected that the effective dosage of the benzimidazole anthelmintic compound when used to treat the conditions disclosed herein will be in the range of from 10 to 5000 mg per day, the compound being administered in one or more discrete dosage units, one or more times to achieve effective therapeutic levels in the patient's cerebral spinal fluid, blood or other infection site for as long as is necessary to treat the condition and maintain the patient free of infection. The precise size, per dose strength, frequency and duration of the dosage regimen will of course depend on the severity of the condition.

SPECIFIC EMBODIMENT OF THE INVENTION

The following example serves to illustrate specific aspects of the invention. Those skilled in the an with readily appreciate that the specific experiments detailed are only illustrative of the invention as described more fully in the claims which follow thereafter.

Eleven benzimidazole derivatives and amphotericin B were tested in vitro against three isolates of *Cryptococcus neoformans*. Drug concentrations inhibiting growth 50% ($IC_{50}$) were determined.

Activity of benzimidazole derivatives and amphotericin B against in vitro growth of three *C.neoformans* isolates are shown in Table I. Inhibitory concentrations were determined by a broth dilution method. All values are in $\mu g/ml$. Yeast were diluted from fresh overnight cultures grown in YEPD at 30° C. to a destiny of $1 \times 10^4$ cells per ml YEPD, and 1 ml portions were aliquoted to culture tubes. Drags were added by two-fold serial dilution. Cultures were incubated at 30° C. with shaking for 20 hrs. Cell numbers were determined with a hemacytometer.

TABLE I

| DRUG | IU4 $IC_{50}$ | IU4 $IC_{90}$ | IU4 $IC_{50}$ | IU4 $IC_{90}$ | IU4 $IC_{50}$ | IU4 $IC_{90}$ |
|---|---|---|---|---|---|---|
| Fenbendazole | 0.019 | 0.028 | 0.011 | 0.014 | <0.016 | <0.016 |
| Nocodazole | 0.13 | 0.22 | 0.09 | 0.12 | 0.20 | 0.29 |
| Parbendazole | 0.16 | 0.23 | 0.16 | 0.23 | 0.16 | 0.22 |
| Mebendazole | 0.23 | 0.43 | 0.18 | 0.32 | 0.19 | 0.40 |
| Albendazole | 0.16 | 0.25 | 0.31 | 0.45 | 0.30 | 0.45 |
| Oxibendazole | 2.3 | 3.2 | 1.0 | 2.1 | 1.4 | 2.1 |
| Carbendazim | 2.0 | 3.6 | 1.5 | 2.0 | 1.6 | 2.3 |
| Benomyl | 2.3 | 3.7 | 2.8 | 3.8 | 2.0 | 3.5 |
| Oxfendazole | 2.5 | >4.0 | 3.2 | >4.0 | 2.8 | >4.0 |
| Thiabendazole | >4.0 | >4.0 | >4.0 | >4.0 | >4.0 | >4.0 |
| Benzimidazole | >4.0 | >4.0 | >4.0 | >4.0 | >4.0 | >4.0 |
| Amphotericin B | 0.035 | 0.064 | 0.024 | 0.065 | 0.011 | 0.045 |

Four derivatives were found to have moderately high activity ($IC_{90}=0.2$–$0.5$ $\mu g/ml$, $IC_{50}=0.1$–$0.3$ $\mu g/ml$), while one, fenbendazole was highly active ($IC_{90}=0.02$–$0.03$ $\mu g/ml$, $IC_{50}=0.1$–$0.2$ $\mu g/ml$). This was 2 fold more active than amphotericin B. Ten additional clinical isolates of *Cryptococcus neoformans* were tested against fenbendazole, mebendazole and albendazole; similar sensitivities were observed.

TABLE II

| DRUG | $IC_{50}$ (range) | $IC_{90}$ (range) |
|---|---|---|
| fenbendazole | 0.012–0.024 | 0.015–0.033 |
| albendazole | 0.12–0.18 | 0.22–0.45 |
| mebendazole | 0.12–0.31 | 0.22–0.45 |

Activity of fenbendazole, albendazole, and mebendazole against in vitro growth of ten *C. neoformans* clinical isolates is shown in Table 2. All values are in μg/ml. $IC_{50}$ and $IC_{90}$ values were comparable to those presented in Table 1, and varied over a narrow range (approximately two-fold).

Cidal activity was tested for two isolates. $LC_{90}$ values were 1.2 μg/ml, $LC_{50}=0.3$ to 1.4 μg/ml for albendazole and mebendazole and 0.06–0.1 μg/ml, $LC_{50}=0.03$ to 0.04 μg/ml for fenbendazole; the latter are about 9 to 13 fold lower than the values obtained for amphotericin B.

TABLE III

| | $LC_{90}$ (μg/ml) | | | |
|---|---|---|---|---|
| Isolate | fenbendazole | albendazole | mebendazole | amphotericin B |
| 1KR | 0.06 | 0.92 | 1.3 | 0.51 |
| 14116 | 0.07 | 2.1 | 2.0 | 0.54 |

In vitro cidal activities of fenbendazole, albendazole, mebendazole, and amphotericin B against two *C. neoformans* isolates are shown in Table 3. Cidal activity was estimated by plating cultures on drug-free medium following a 20 h. incubation in the presence of different drug concentrations. Activity is expressed as $LC_{90}$, the concentration resulting in 90% reduction in cell number relative to the starting (t=0) number.

Spontaneous resistance to 1 μg/ml fenbendazole occurred at a frequency of $<1\times10^{-7}$; the corresponding frequency for amphotericin B was approximately $2\times10^{-6}$.

TABLE 4

```
                 *           120           *           140           *           160
         TEGAELVDSVLDVVRREAERCDCLQGFQITHSLGGGTGAGMGTLLISKIREEFPDRMMCTFSV
CNBTB    ............................................................
PCBT     .........N.V...........A....................................Y..A..
ANBENA   ...............G....S..L................................I.N....
HUTUBBM  ...............K.G....L..................................I.SS...
CEBEN1   ...............K.G....L.S.................................I.SS...
CETUB1   .............I.K.G....L.S.................................Y.I.SS...
ANTUBB   ...............Q.I....S..A.V.S............................Y.I.A..
CEMEC7   ...............K.ST...L..S................................Y.I.N...
CABT     ............M.I.......G.S..S.................F....K.L.....T..A..
SCBT     ...............LQQ..NS.S..................................Y.....
CNBTA    .............P..........VL...S..LA..LG......Y..LA..I

*           180           *           200           *           220
         VPSPKVSDTVVEPYNATLSVHQLVENSDETFCIDNEALYDICLRTLKLSTPTYGDLNHLVSVV
CNBTB    ............................................................
PCBT     ..........................................M..PD.G........A.
ANBENA   ..............................H..T..........M.N.S........AT
HUTUBBM  ..............................T..Y..........F..T.........T
CEBEN1   ....R.........................T..Y..........F..T.N........T
CETUB1   ....R.........................T..Y..........Y..TN.........LT
ANTUBB   .M............................H..S..........I..S.S.......A.
CEMEC7   ....R.........................T..S..........F..T.........AT
CABT     ......................................N.QN..PQ.S.AE.N..S.
SCBT     .L..T.......................I................Q..NQ.S..N.S.
CNBTA    .F......V.T.N.........H....I.C..........N.VSD.IQS.E.K..S.IAK.

*           240           *           260
         MSGVTTCLRFPGQLNSDLRKLAVNMVPF
CNBTB    ............................
PCBT     ..I.........................
ANBENA   .............W..............
HUTUBBM  ...............A............
CEBEN1   ...............A............
CETUB1   ...............A............
ANTUBB   ..I.VS.........A............
CEMEC7   ............................
CABT     .........S..Y...........L...
SCBT     .........S..Y...........L...
CNBTA    .T.F.....?????.V............
```

| | % Identity | Benzimidazole S? |
|---|---|---|
| CNBTB | 100 | S |
| PCBT | 94 | S |
| ANBENA | 94 | R |
| HUTUBBM | 91 | S |
| CEBEN1 | 90 | R |
| CETUB1 | 88 | S |
| ANTUBB | 88 | R |
| CEMEC7 | 89 | S |
| CABT | 88 | S ? |
| SCBT | 86 | S |
| CNBTA | 72 | R ? |

Alignment of β-tubulin residues 107–260 is shown in Table 4. Dots represent identity to the CNBTB sequence. Arrows indicate residues responsible for benomyl or thiabendazole resistance in *S. cerevisiae* (R241 to H), *N.crassa* (F167 to Y), and *A. nidulans* (A165 to V; E198 to D, N, or K; F200 to Y). The sequences are from *C. neoformans* (CNBTB and CNBTA), *P. carinii* (PCBT), *A. nidulans* (ANBENA and ANTUBB), a human (HUTUBBM), *C. elegans* (CEBEN1, CETUB 1, and CEMEC7), *C. albicans* (CABT), and *S. cerevisiae* (SCBT). Tubulins are labelled S if they are sensitive to any benzimidazole, R if they are resistant to all benzimidazoles (CABT appears sensitive when expressed in *S. cerevisiae*, but this could be artifactual).

The alignment of β-tubulin residues (Table 4) permits the calculation of the similarity (% identity) of the two *C. neoformans* β-tubulins (CNBTB and CNBTA) to other previously published β-tubulins, several of which are shown. These calculations confirm that *C. neoformans* CNBTB β-tubulin is indeed very similar to other fungal β-tubulins, such as *Aspergillus nidulans* benA. This alignment also permits us to determine if specific amino acids (positions 167, 198, 200, and 241 ) that have been previously implicated in sensitivity to the antifungal benzimidazole benomyl are present in *C. neoformans* β-tubulin. These are indeed present in CNBTB; in particular, amino acid 200 (F) is highly correlated with benzimidazole sensitivity in fungi (such as ANBENA), helminths (such as CEBEN 1 ), and protozoa. One additional amino acid (position 165) has been previously implicated in sensitivity to the anthelminthic/antifungal benzimidazole thiabendazole. Position 165 is variable among many β-tubulins examined. There is currently no data that identifies amino acid positions specifically involved in sensitivity to anthelminthic benzimidazoles such as albendazole and fenbendazole. However, we predict that the presence of c at position 165 in CNBT is partly responsible for the unexpected sensitivity of *C. neoformans* to these anthelminthic benzimidazoles.

Conclusions

Benzimidazoles fall into four groups on the basis of activity versus *C. neoformans* (Table 1 ). Fenbendazole is highly active ($IC_{50}=0.02$ μg/ml), the carbendazim group is weakly active ($IC_{50}=2$ μg/ml) and thiabendazole is inactive at the highest concentration tested. In comparison to amphotericin B, the currently recommended anticryptoccocal agent, the albendazole group was generally 5–10 less inhibitory and 2–4 less cidal, but fenbendazole was 2–3fold more inhibitory and 8–9 fold more cidal.

The high inhibitory and cidal activities of certain benzimidazoles against *C.neoformans* suggest that this group may provide a new therapeutic approach to cryptococcocal meningitis. The route of administration of benzimidazoles is oral, a clear advantage over amphotericin B. However, benzimidazoles derivatives vary in their intestinal absorption. Penetration of benzimidazoles into the central nervous system has not been well studied. However, in hums with neurocysticercosis, and oral dose of 15 mg/kg resulted in albendazole levels in CSF of about 0.4 μg/ml, which exceeds the $IC_{50}$ for most of the *C.neoformans* strains tested.

Since clinical usefulness of a drug may be limited by the frequency at which spontaneous resistance occurs, this frequency was estimated in vitro. Mutants resistant to 5 μg/ml albendazole or mebendazole occured at frequencies of $<3\times10^6$; resistance to 1 μg/ml fenbendazole occured at a frequency of only $5\times10^9$.

Our current investigations of the mechanism of action of these drugs against *C. neoformans* are focused on the characterisation of tubulin genes from wild type *C. neoformans* and benzimidazole resistant mutants. Fragments of two β-tubulin genes from *C.neoformans* have been cloned, and sequencing has identified amino acid residues previously implicated in benzimidazole actively.

What is claimed is:

1. A method of treatment of *Cryptococcus neoformans* infection which comprises administering to a patient in need thereof an effective amount of a benzimidazole compound selected from the group consisting of fenbendazole, albendazole, mebendazole, oxfendazole, parbendazole, cambendazole, flubendazole, ricobendazole and luxabendazole, or a prodrug thereof.

2. A method according to claim 1 in which the benzimidazole compound is selected from the group consisting of fenbendazole, albendazole and mebendazole.

3. A method of treatment of meningitis caused by *Cryptococcus neoformans* infection in AIDS patients which comprises administering to a patient in need thereof an effective amount of a benzimidazole compound selected from the group consisting of fenbendazole, albendazole, mebendazole, oxfendazole, parbendazole, cambendazole, flubendazole, ricobendazole and luxabendazole, or a prodrug thereof.

4. A method according to claim 3 in which the benzimidazole compound is selected from the group consisting of fenbendazole, albendazole and mebendazole.

5. A method according to claim 2 in which the benzimidazole compound is albendazole.

6. A method according to claim 4 in which the benzimidazole compound is albendazole.

* * * * *